(12) United States Patent
Budidet et al.

(10) Patent No.: US 8,492,551 B2
(45) Date of Patent: Jul. 23, 2013

(54) PROCESS FOR PREPARING AN OPTICALLY ACTIVE PROTON PUMP INHIBITOR

(75) Inventors: Shankar Reddy Budidet, Hyderabad (IN); Brajesh Kumar Sinha, Hyderabad (IN); Somappa Somannavar Yallappa, Hyderabad (IN); Senthil Kumar Natarajan, Hyderabad (IN); Ramesh Dandala, Hyderabad (IN); Sivakumaran Meenakshisunderam, Hyderabad (IN)

(73) Assignee: Aurobindo Pharma. Ltd., Hyderabad (IN)

( * ) Notice: Subject to any disclaimer, the term of this patent is extended or adjusted under 35 U.S.C. 154(b) by 578 days.

(21) Appl. No.: 12/451,871

(22) PCT Filed: May 30, 2008

(86) PCT No.: PCT/IB2008/001427
§ 371 (c)(1),
(2), (4) Date: Dec. 5, 2009

(87) PCT Pub. No.: WO2008/149204
PCT Pub. Date: Dec. 11, 2008

(65) Prior Publication Data
US 2010/0125142 A1 May 20, 2010

(30) Foreign Application Priority Data
Jun. 7, 2007 (IN) .......................... 1174/CHE/2007

(51) Int. Cl.
*C07D 401/12* (2006.01)
(52) U.S. Cl.
USPC .................................................... 546/273.7
(58) Field of Classification Search
USPC .................................................... 546/273.7
See application file for complete search history.

(56) References Cited

U.S. PATENT DOCUMENTS

| | | | |
|---|---|---|---|
| 4,255,431 A | 3/1981 | Junggren et al. |
| 4,738,974 A | 4/1988 | Brandstrom |
| 5,693,818 A | 12/1997 | Von Unge |
| 5,948,789 A | 9/1999 | Larsson et al. |
| 6,369,085 B1 | 4/2002 | Cotton et al. |
| 7,169,793 B2 | 1/2007 | Reddy et al. |
| 7,777,044 B2 | 8/2010 | Coppi et al. |
| 7,888,511 B2 | 2/2011 | Ha et al. |
| 2008/0167473 A1 | 7/2008 | Coppi et al. |
| 2010/0113526 A1 | 5/2010 | Rao et al. |
| 2010/0160639 A1 | 6/2010 | Singh et al. |

FOREIGN PATENT DOCUMENTS
CN 1223262 7/1999

OTHER PUBLICATIONS

Kirk-Othmer Encyclopedia of Chemical Technology, vol. 8, p. 95-147 (2002).*
Yu et al., "Physical characterization of, etc.," PSTT, vl. 1(3), 118-127 (1998).*
Vippagunta et al., "Crystalline Solids", Advanced Drug Delivery Reviews 48 (2001) 3-26.*
Deng J. et al, Resolution of omeprazole by inclusion complexation with a chiral host BINOL,Tetrahedron: Asymmetry 11 (2000) pp. 1729-1732, Elsevier Science Ltd.

* cited by examiner

*Primary Examiner* — Patricia L Morris
(74) *Attorney, Agent, or Firm* — Jay R Akhave

(57) ABSTRACT

An improved process for the preparation of (S)-5-methoxy-2-[[(4-methoxy-3,5-dimethyl-2-pyridinyl)methyl]sulfinyl]-1H-benzimidazole of Formula I, (I) with high enantiomeric excess from racemic mixture.

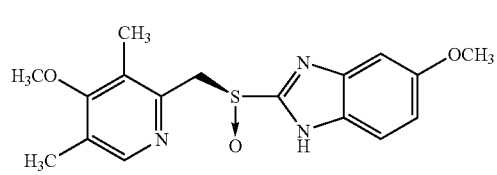

(I)

12 Claims, No Drawings

PROCESS FOR PREPARING AN OPTICALLY ACTIVE PROTON PUMP INHIBITOR

FIELD OF THE INVENTION

The present invention relates to an improved process for the preparation of (S)-5-methoxy-2-[[(4-methoxy-3,5-dimethyl-2-pyridinyl)methyl]sulfinyl]-1H-benzimidazole of Formula I, Formula I

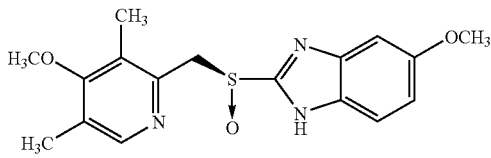

with high enantiomeric excess from racemic mixture.

BACKGROUND OF THE INVENTION (S)-5-Methoxy-2-[[(4-methoxy-3,5-dimethyl-2-pyridinyl)methyl]sulfinyl]-1H-benzimidazole of Formula I, which is generically known as Esomeprazole, is a Proton Pump Inhibitor. Esomeprazole Magnesium is being marketed under the Trade name NEXIUM as Delayed Release Capsules. Esomeprazole Sodium is also being marketed under the Trade name NEXIUM IV as an Intravenous Injection.

Esomeprazole is used for inhibiting gastric acid secretion in mammals and man. In a more general sense, esomeprazole is used for the treatment of gastric acid-related diseases and gastrointestinal inflammatory diseases in mammals and man, such as gastric ulcer, duodenal ulcer, reflux esophagitis, and gastritis.

Several processes to prepare esomeprazole have been disclosed in the prior-art, some of which are summarized below:

U.S. Pat. No. 5,693,818 discloses a process to prepare esomeprazole by separating a diastereomeric ester of omeprazole, having either R or S configuration and dissolving each of the separated diastereomers in an alkaline solution of above pH 7 so as to hydrolyze the acyloxymethyl group from the separated diastereomers to give the optically pure enantiomers which are neutralized with a neutralizing agent which can be an acid or an ester and the pH being maintained at or above 7 throughout the process to yield esomeprazole.

U.S. Pat. No. 5,948,789 discloses a process to prepare esomeprazole, by reacting prochiral sulphide with cumene hydroperoxide in the presence of diethyl tartrate, titanium isopropoxide and amine. A disadvantage of this method is that the strict control on reaction conditions and quantities of oxidizing agents has to be maintained to avoid over oxidation of desired sulfoxide to sulfone impurity. Moreover, these methods require expensive reagents like titanium isoperoxide and diethyl tartarate.

CN 1223262 A discloses a process to prepare esomeprazole, by dissolving racemic omeprazole and (S)-(−)-[1,1'-Binaphthalene]-2,2'-diol (BINOL) in a mole ratio of 1:0.5-2 at a temperature of 60-130° C. in a solvent system such as benzene, toluene, dimethylbenzene and trimethylbenzene or acetonitrile for 12-72 h. The inclusion complex of esomeprazole and BINOL is subjected to conventional chromatographic separation to obtain optically pure esomeprazole. The reaction is carried out for longer periods, which is commercially not desirable. The maximum enantiomeric excess achieved by the above process is very low, approximately 80%.

WO 2006/094904 A1 discloses a process to prepare esomeprazole, which comprises treating the racemic mixture of omeprazole with BINOL in a molar ratio of 1:0.5-3, in a mixture of an amine and organic solvent to yield inclusion complex. The inclusion complex was treated with a hydroxide of an alkaline metal in a mixture of water and toluene to give optically pure esomeprazole. However, this process has yielded an inclusion complex of esomeprazole and BINOL with 95.7% of maximum enantiomeric excess, which requires further purification to achieve 99.7% enantiomeric excess, but this accompanied a yield loss of about 38% of inclusion complex.

WO 2007/013743 A1 discloses a process to prepare esomeprazole, which comprises treating the racemic mixture with BINOL with molar ratio of 1:0.5-0.7, in a mixture of a weak base, water and alcoholic solvent to yield the inclusion complex. The inclusion complex was treated with a hydroxide of an alkaline metal in water to give optically pure esomeprazole. However, the process yielded an inclusion complex of esomeprazole and BINOL having enantiomeric excess 96.8%, which requires further purification to achieve 99.4% enantiomeric excess, but this accompanied a yield loss of about 12% of inclusion complex.

In view of the above, it is desired to have a commercially viable process to prepare esomeprazole with high enantiomeric excess.

We have now found that by treating omeprazole with aromatic or polyaromatic phenols and optionally substituted phenols in the presence of BINOL yields esomeprazole with enhanced enantiomeric excess of greater than 98% and with a good quality. Further, the invention does not require any purification of esomeprazole-BINOL inclusion complex and carried out further reactions to yield esomeprazole with higher enantiomeric excess.

Objective

The objective of the present invention is to provide an improved process for preparing optically pure esomeprazole with good quality and purity.

In yet another objective of the present invention is to provide an improved process for preparing esomeprazole, which is simple, industrially applicable and economically viable.

SUMMARY OF THE INVENTION

The present invention relates to an improved process for preparing esomeprazole of Formula I, Formula I

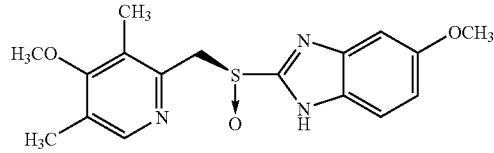

which comprises:
a) treating omeprazole with BINOL and an aromatic or polyaromatic phenol;
b) isolating the esomeprazole-BINOL inclusion complex; and
c) converting the esomeprazole-BINOL inclusion complex in a solvent to give esomeprazole; and d) optionally converting esomeprazole into its salts and hydrates thereof.

DETAILED DESCRIPTION OF THE INVENTION

BINOL as used herein refers to S-(−)-1,1'-binaphthol. The aromatic or polyaromatic phenol as used herein refers to phenol, substituted phenol, naphthol, substituted naphthol, wherein substitution on phenol or naphthol is selected from hydroxy, thio, halo, nitro, amino, alkylamino, arylamino, alkyl, cycloalkyl, amido, carboxylic, carboxyl, thioalkyl, thioaryl.

A mixture of BINOL and an aromatic or polyaromatic phenol is brought to a temperature of 0-120° C. The mixture can be prepared in the presence or absence of a solvent. Omeprazole is added to this reaction mixture at 0-120° C. Thereafter, the reaction mixture is cooled to 20-30° C. if the reaction mixture temperature is 35-120° C. If the temperature of the reaction mixture is between 0-15° C., then the reaction mixture is heated to 20-30° C. The reaction mixture is seeded with esomeprazole-BINOL inclusion complex at 20-30° C. and stirred for approximately 3 h to crystallize the product. To this reaction mass an antisolvent is added and stirred for 1-15 h at 20-30° C. for complete crystallization of esomeprazole-S-(−)-binaphthol inclusion complex product.

A mixture of BINOL and aromatic or polyaromatic phenol is heated for 30 min at 50-75° C. The mixture is prepared in presence or absence of a solvent. Omeprazole is added to this reaction mixture at 40-50° C. and stirred for 30 min. The reaction mixture is seeded with esomeprazole-S-(−)-binaphthol inclusion complex and stirred for 2 h to crystallize the product. To this reaction mass an antisolvent is added and slurried for 1-15 h at 20-30° C. for complete crystallization of esomeprazole-S-(−)-binaphthol inclusion complex product.

A mixture of BINOL and aromatic or polyaromatic phenol is heated to a temperature of 50-75° C. for 30 min. The mixture is prepared in the presence or absence of a solvent. Omeprazole is added to the reaction mixture at 40-50° C. and stirred for 30 min. The reaction mixture is seeded with esomeprazole-BINOL inclusion complex and cooled to 20-30° C. Then the reaction mass is stirred for 2 h to crystallize the product. To this reaction mass an antisolvent is added and stirred for 1-15 h at 20-30° C. for complete crystallization of esomeprazole-S-(−)-binaphthol inclusion complex.

A mixture of BINOL and aromatic or polyaromatic phenol is treated at a temperature 20-30° C. The mixture is prepared in the presence or absence of a solvent. Omeprazole is added to the reaction mixture and seeding the reaction mixture with esomeprazole-BINOL inclusion complex. Then the reaction mixture is stirred for 2 h to crystallize the product. To this reaction mass an antisolvent is added and stirred for 1-15 h at 20-30° C. for complete crystallization of esomeprazole-S-(−)-binaphthol inclusion complex.

A mixture of BINOL and aromatic or polyaromatic phenol is treated at a temperature 50-75° C. for 30 min. The mixture is prepared in presence or absence of a solvent. Omeprazole is added in to the reaction mixture at 40-50° C. and stirred for 10 min. The reaction mixture is seeding with esomeprazole-BINOL inclusion complex. Thereafter, reaction mixture is cooled to 20-30° C. and stirred for 2 h to crystallize the product. To this reaction mass an antisolvent is added and stirred for 1-15 h at 20-30° C. for complete crystallization of esomeprazole-S-(−)-binaphthol inclusion complex product as a white solid.

The solvent as used herein is selected from the group consisting of aprotic solvent, such as esters, ethers, ketones, nitriles, hydrocarbons, chlorinated hydrocarbons; polar aprotic solvents, such as dimethylformamide, dimethylsulfoxide; polar solvents, such as alcohols, water and mixtures thereof.

The antisolvent as used herein is selected from the group consisting of aprotic solvent, such as esters, ketones, ethers, nitriles, hydrocarbons, chlorinated hydrocarbons; polar solvents, such as alcohols, water and mixtures thereof.

The esters such as ethyl acetate, n-butyl acetate; ethers such as methyl t-butyl ether, diethylether, dimethylether, diisopropylether; tetrahydrofuran; ketones such as acetone, 2-butanone, and 4-methylpentan-2-one; nitriles such as acetonitrile; hydrocarbons such as benzene, toluene, heptane, hexane; chlorinated hydrocarbons such as carbon tetrachloride, methylene dichloride, chloroform; alcohols such as methanol, ethanol, propanol, butanol, isopropyl alcohol, 1-propanol.

The major advantage realized with the process of the present invention is isolation of esomeprazole-BINOL inclusion complex as a white solid in good enantiomeric excess, whereas the prior-art processes produce a colored esomeprazole-BINOL inclusion complex, and with lower enantiomeric excess. The esomeprazole salt obtained through white esomeprazole-BINOL inclusion complex has high purity and greater enantiomeric excess; greater than 99.9%.

The esomeprazole-BINOL inclusion complex is dissolved in a solvent and in the presence of organic and inorganic base selected from ammonia, triethyl amine, diisopropylethyl amine, sodium bicarbonate, sodium hydroxide, potassium hydroxide; alkali and alkaline earth metal selected from sodium methoxide, lithium methoxide, sodium ethoxide, lithium ethoxide, sodium metal; acid salts selected from sodium acetate, lithium acetate, potassium acetate. The aqueous layer is separated from the organic layer and thoroughly washed with a solvent. The aqueous layer is mixed with a solvent and pH of the reaction mixture is adjusted using an acid to yield esomeprazole. Acid is selected from hydrochloric acid, acetic acid, sulphuric acid; solvent is selected from aprotic solvent, such as esters, ethers, nitriles, hydrocarbons, chlorinated hydrocarbons; polar aprotic solvents, such as dimethylformamide, dimethylsulfoxide; polar solvents, such as alcohols, water and mixtures thereof.

The esters are selected from ethyl acetate, n-butyl acetate; ethers are selected from methyl t-butyl ether, diethylether, dimethylether, diisopropylether, tetrahydrofuran; nitriles are selected from acetonitrile; hydrocarbons are selected from benzene, toluene, heptane, hexane; chlorinated hydrocarbons are selected from carbon tetrachloride, methylene dichloride, chloroform; alcohols are selected from methanol, ethanol, propanol, butanol, isopropyl alcohol, 1-propanol.

The esomeprazole-BINOL inclusion complex is dissolved in a solvent and in the presence of organic and inorganic base selected from ammonia, triethyl amine, diisopropylethyl amine, sodium bicarbonate, sodium hydroxide, potassium hydroxide; alkali and alkaline earth metal selected from sodium methoxide, lithium methoxide, sodium ethoxide, lithium ethoxide, sodium metal; acid salts selected from sodium acetate, lithium acetate, potassium acetate. The aqueous layer is separated from the organic layer and thoroughly washed with a solvent. Thereafter, to the aqueous layer 20% w/w aqueous ammonium formate solution is added and extracted with a solvent. Solvent is selected from aprotic solvent, such, as esters, ethers, nitriles, hydrocarbons, chlorinated hydrocarbons; polar aprotic solvents, such as dimethylformamide, dimethylsulfoxide; polar solvents, such as alcohols, water and mixtures thereof. The layers were separated and the organic layer is washed with water and concentrated under reduced pressure to yield a foamy mass. The concentrated mass was dissolved in ethyl acetate and cooled to <5° C. To the solution alkali and alkaline earth metal selected from sodium methoxide, lithium methoxide, sodium ethoxide, lithium ethoxide, sodium metal is added and stirred at 20-30° C. for 90 min to 120 min to yield esomeprazole sodium. This is further converted to esomeprazole magnesium.

The BINOL used in the process is recovered from the extractions and can be recycled for further use.

The chiral purity of esomeprazole obtained by the process of the present is found out by using a Silica gel AGP column for chiral chromatography (100×4.0 mm) 5μ and a mobile phase—Acetonitrile R, phosphate buffer solution pH 6 (65: 435 v/v); flow rate 0.6 ml/min and is detected at 302 nm.

The esomeprazole, which is prepared by the above process, can be further converted into its pharmaceutically acceptable salts and hydrates thereof.

The esomeprazole magnesium prepared by the process of the present invention can be anhydrate or hydrate, specifically trihydrate. The product can amorphous or crystalline or partially crystalline in nature.

The esomeprazole is effective as a gastric acid secretion inhibitor, and is useful as an antiulcer agent. Any suitable route of administration may be employed for providing the patient with an effective dosage of the esomeprazole. For example, oral, parenteral, subcutaneous, intramuscular, rectal, transdermal and the like may be employed. Dosage forms include capsules, tablets, dispersions, suspensions, solutions and the like.

The pharmaceutical compositions of the present invention comprise the esomeprazole as active ingredient, or a pharmaceutically acceptable salt thereof, and may also contain a pharmaceutically acceptable carrier and optionally other therapeutic ingredients. The term "pharmaceutically acceptable salt" refers to both acid and alkaline pharmaceutically acceptable non-toxic salts. Compositions comprising other therapeutic ingredients are especially of interest in the treatment of Helicobacter infections. The compositions include compositions suitable for oral, rectal or parenteral such as subcutaneous, intramuscular, and intravenous administration. The most preferred route of the present invention is the oral route. The compositions may be conveniently presented in unit dosage forms, and prepared by any methods well known in the art of pharmacy. The most suitable route of administration as well as the magnitude of a therapeutic dose of the esomeprazole or a pharmaceutically acceptable salt thereof in any given case will depend on the nature and severity of the disease to be treated.

The invention is illustrated with the following examples, which are provided by way of illustration only and should not be construed to limit the scope of the invention.

EXAMPLE 1

Preparation of Esomeprazole-BINOL Inclusion Complex

BINOL (6.63 g; 23.16 mmol) and phenol (4.09 g; 43.46 mmol) were added to toluene (70 ml) and heated the mixture to 75° C. to obtain clear solution. Omeprazole (10 g; 28.95 mmol) was added to the reaction mass at 45° C. and stirred for 10 min at 40-45° C. Thereafter, the reaction mass was seeded with esomeprazole-BINOL inclusion complex. The reaction mass was cooled and stirred for 2 h at 20-30° C. to crystallize the product. Then, hexane (35 ml) was added to the reaction mass and stirred for 15 h at 20-30° C. for complete crystallization of title compound, which was filtered and washed with toluene-hexane mixture and dried to obtain white solid of esomeprazole-BINOL inclusion complex.

Yield—7.5 g (82%)
Enantiomeric excess—98.24%.

EXAMPLE 2

Preparation of Esomeprazole-BINOL Inclusion Complex

BINOL (6.22 g; 21.72 mmol) and phenol (4.09 g; 43.46 mmol) were added to toluene (70 ml) at 20-30° C. Omeprazole (10 g; 28.95 mmol) was added to the reaction mixture and seeded with esomeprazole-BINOL inclusion complex. Thereafter, the reaction mass was stirred for 2 h to crystallize the product. Then, hexane (35 ml) was added to the reaction mass and stirred for 15 h at 20-30° C. for complete crystallization of title compound, which was filtered, washed with toluene-hexane mixture and dried to obtain white solid of esomeprazole-BINOL inclusion complex.

Yield—7.98 g (87.3%)
Enantiomeric excess—98.3%.

EXAMPLE 3

Preparation of Esomeprazole-BINOL Inclusion Complex

BINOL (31.08 g; 108.54 mmol) and phenol (20.4 g; 216.76 mmol) were added to toluene (350 ml) at 20-30° C. Omeprazole (50 g; 144.75 mmol) was added to the reaction mixture and seeded with esomeprazole-BINOL inclusion complex. The resulting reaction mixture was stirred for 3 h to crystallize the product. Heptane (210 ml) was added to the reaction mass and stirred for 3 h at 20-30° C. for complete crystallization of title compound, which was filtered, washed with toluene-heptane mixture and dried to obtain white solid of esomeprazole-BINOL inclusion complex.

Yield—37.7 g (82.45%)
Enantiomeric excess—98%.

EXAMPLE 4

Preparation of Esomeprazole-BINOL Inclusion Complex

BINOL (1.95 g; 6.81 mmol) and 2-naphthol (3.13 g; 21.71 mmol) were added to toluene (100 ml) and heated the mixture to 60° C. to obtain clear solution. Omeprazole (5 g; 14.47 mmol) was added to the solution at 55° C. and stirred for 10 min at 50-55° C. The reaction mixture was seeded with esomeprazole-BINOL inclusion complex and thereafter cooled and stirred for 2 h at 20-30° C. to crystallize the product. Hexane (50 ml) was added to the reaction mass and stirred for 15 h at 20-30° C. for complete crystallization of title compound, which was filtered, washed with toluene-hexane mixture and dried to obtain white solid of esomeprazole-BINOL inclusion complex.

Yield—3.05 g (66.7%)
Enantiomeric excess—98.44%.

EXAMPLE 5

Preparation of Esomeprazole-BINOL Inclusion Complex

BINOL (2.5 g; 8.73 mmol) and 2-naphthol (2.61 g; 18.103 mmol) were added to toluene (100 ml) and heated the mixture to 60° C. to obtain clear solution. Omeprazole (5 g; 14.47 mmol) was added to the solution at 55° C. and stirred for 10 min at 50-55° C. The reaction mixture was seeded with esomeprazole-BINOL inclusion complex and thereafter cooled and stirred for 2 h at 20-30° C. to crystallize the product. Hexane (50 ml) was added to the reaction mass and stirred for 15 h at 20-30° C. for complete crystallization of title compound, which was filtered, washed with toluene-hexane mixture and dried to obtain white solid of esomeprazole-BINOL inclusion complex.

Yield—3.65 g (79.86%)

Enantiomeric excess—98.16%.

EXAMPLE 6

Preparation of Esomeprazole-BINOL Inclusion Complex

BINOL (5 g; 17.462 mmol) and 2-naphthol (6.26 g; 43.42 mmol) were added to toluene (200 ml) and heated the mixture to 60° C. to obtain a clear solution. Omeprazole (10 g; 28.95 mmol) was added to the solution at 55° C. and stirred for 10 min at 50-55° C. The reaction mixture was seeded with esomeprazole-BINOL inclusion complex and thereafter cooled and stirred for 2 h at 20-30° C. to crystallize the product. Hexane (100 ml) was added to the reaction mass and stirred for 6 h at 20-30° C. for complete crystallization of title compound, which was filtered, washed with toluene-hexane mixture and dried to obtain white solid of esomeprazole-BINOL inclusion complex.

Yield—6.4 g (69.7%)

Enantiomeric excess—98.28%.

EXAMPLE 7

Preparation of Esomeprazole-BINOL Inclusion Complex

BINOL (1.66 g; 5.79 mmol) and phenol (0.27 g; 2.86 mmol) were added to toluene (30 ml) at 20-30° C. and heated the mixture to 55° C. Omeprazole (2 g; 5.79 mmol) was added to the mixture and stirred at 50-55° C. for 30 min. The solution was cooled to 30° C. and seeded with esomeprazole-BINOL inclusion complex. The reaction mixture was stirred for 2 h to crystallize the product. To this mass, hexane (15 ml) was added and stirred for 15 h at 20-30° C. for complete crystallization of title compound, which was filtered, washed with toluene-hexane mixture, and dried to obtain a white solid of esomeprazole-BINOL inclusion complex.

EXAMPLE 8

Preparation of Esomeprazole-BINOL Inclusion Complex

BINOL (4.14 g; 14.47 mmol) and phenol (1.36 g; 14.47 mmol) were added to toluene (100 ml) at 20-30° C. and heated the mixture to 45° C. Omeprazole (5 g; 14.47 mmol) was added to the mixture and stirred at 40-45° C. for 30 min. The solution was cooled to 20-30° C. and stirred for 2 h to crystallize the product. Hexane (50 ml) was added to the reaction mass and stirred for 15 h at 20-30° C. for complete crystallization of title compound, which was filtered, washed with toluene-hexane mixture and dried to obtain white solid of inclusion complex of esomeprazole-BINOL.

EXAMPLE 9

Preparation of Esomeprazole-BINOL Inclusion Complex

BINOL (1 g; 3.49 mmol) and phenol (0.545 g; 5.79 mmol) were added to the mixture of ethanol (16 ml) and water (4 ml) at 20-30° C. and heated the mixture to 45° C. Omeprazole (2 g; 5.79 mmol) was added to the mixture and stirred at 40-45° C. to obtain a clear solution. The solution was cooled to 30° C. and seeded with esomeprazole-BINOL inclusion complex. The mixture was stirred for 15 h at 20-30° C. for complete crystallization of title compound, which was filtered, washed with mixture of water-ethanol (1:1) and dried to obtain off-white solid of esomeprazole-BINOL inclusion complex.

EXAMPLE 10

Preparation of Esomeprazole-BINOL Inclusion Complex

BINOL (1.95 g; 6.81 mmol) and phenol (2.04 g; 21.68 mmol) were added to toluene (100 ml) and heated the mixture to 60° C. to obtain clear solution. Omeprazole (5 g; 14.47 mmol) was added to the solution at 55° C. The reaction mixture was stirred at 50-55° C. for 10 min and seeded with esomeprazole-BINOL inclusion complex. Further, the reaction mixture was stirred for 2 h at 20-30° C. to crystallize the product. To this reaction mass hexane (50 ml) was added and stirred for 15 h at 20-30° C. for complete crystallization of title compound, which was filtered, washed with toluene-hexane mixture and dried to obtain white solid of esomeprazole-BINOL inclusion complex.

EXAMPLE 11

Preparation of Esomeprazole-BINOL Inclusion Complex

BINOL (5 g; 17.462 mmol) and phenol (4.08 g; 43.35 mmol) were added to toluene (200 ml) and heated the mixture to 60° C. to obtain clear solution. Omeprazole (10 g; 28.95 mmol) was added to the solution at 55° C. and stirred for 10 min at 50-55° C. Thereafter, the reaction mass was seeded with esomeprazole-BINOL inclusion complex. The reaction mass was cooled and stirred for 2 h at 20-30° C. to crystallize the product. To this reaction mass hexane (100 ml) was added and stirred for 15 h at 20-30° C. for complete crystallization of title compound, which was filtered, washed with toluene-hexane mixture and dried to obtain white solid of esomeprazole-BINOL inclusion complex.

EXAMPLE 12

Preparation of Esomeprazole-BINOL Inclusion Complex

BINOL (6.22 g; 21.72 mmol) and phenol (4.09 g; 43.46 mmol) were added to toluene (70 ml) at 20-30° C. Omeprazole (10 g; 28.95 mmol) was added to the reaction mixture and seeded with esomeprazole-BINOL inclusion complex. The reaction mixture was stirred for 3 h to crystallize the product. To this reaction mass heptane (52.5 ml) was added and stirred for 3 h at 20-30° C. for complete crystallization of title compound, which was filtered, washed with toluene-heptane mixture and dried to obtain white solid of esomeprazole-BINOL inclusion complex.

EXAMPLE 13

Preparation of Esomeprazole-BINOL Inclusion Complex

BINOL (15.54 g; 54.27 mmol) and omeprazole (25 g; 72.38 mmol) were added to phenol (20.44 g) at 20-30° C. Thereafter, the reaction mixture was seeded with esomeprazole-BINOL inclusion complex and stirred for 3 h to crystallize the product. To this reaction mass a mixture of hexane and toluene (0.6:1 v/v; 280 ml) was added and stirred for 15 h at 20-30° C. for complete crystallization of title compound, which was filtered and washed with hexane-toluene mixture (0.6:1; 20 ml) and dried to obtain white solid of esomeprazole-BINOL inclusion complex.

EXAMPLE 14

Preparation of Esomeprazole

Esomeprazole-BINOL inclusion complex (100 g; 158.29 mmol; ee of 98.28%) was suspended in methyl t-butyl ether (1300 ml). Aqueous sodium hydroxide solution (2.2% w/w; 302 g) was added to the suspended mass at 20-30° C. and stirred till clear solution was obtained. Thereafter, organic layer was separated and the aqueous layer was extracted with methyl t-butyl ether for recovery of BINOL. The organic layers were combined, concentrated and recovered 44.4 g of BINOL. To the aqueous layer, methylene chloride (300 ml) was added and pH was adjusted to 7-8 with 10% v/v aqueous acetic acid. The organic layer was separated and washed with DM water and concentrated under reduced pressure to yield esomeprazole as a foamy solid mass.

Yield—54.5 g

Enantiomeric excess—98.1%.

EXAMPLE 15

Preparation of Esomeprazole Sodium

Esomeprazole obtained in example 14 (54.5 g; 157.78 mmol), was dissolved in a solution of aqueous NaOH (136.24 g; 4.88% w/w) and DM water (30 ml). The solution was washed with methylene chloride twice (200 ml×2). The aqueous layer was filtered and concentrated completely under reduced pressure to yield viscous mass. Ethanol was added to the viscous mass and concentrated under reduced pressure. Thereafter, ethyl acetate was added and concentrated to dryness under reduced pressure to yield solid mass. Further, ethyl acetate (400 ml) was added and stirred the mixture under reflux for 30 min. Cooled the reaction mass to 20-30° C. and stirred for 3 h. The separated solid was filtered, washed with ethyl acetate and dried under reduced pressure at 40° C. to yield esomeprazole sodium.

Yield—50.6 g (87%)

Enantiomeric excess—99.96%.

EXAMPLE 16

Preparation of Esomeprazole Sodium

Esomeprazole-BINOL inclusion complex (100 g; 158.3 mmol; ee of 98.2%) was suspended in a mixture of methyl t-butyl ether (1300 ml) and DM water (400 ml). Aqueous sodium hydroxide solution (5 w/w; 133 g) was added to the suspended mass at 20-30° C. and stirred till clear solution was obtained. Thereafter, organic layer was separated and the aqueous layer was washed with methyl t-butyl ether. Thereafter, 20% aqueous ammonium formate solution (60 ml) was added and extracted with methylene chloride (300 ml). The organic layer was washed with DM water and concentrated under reduced pressure to yield a foamy mass. The concentrated mass was dissolved in ethylacetate (400 ml) and cooled to 0-5° C. To the solution, sodium ethoxide (10.77 g, mmol) was added and stirred at 20-30° C. for 90 min. The separated solid mass was filtered, washed with ethyl acetate and dried under reduced pressure at 40° C. to yield esomeprazole sodium.

Yield—50.6 g

Enantiomeric excess—99.96%.

EXAMPLE 17

Preparation of Esomeprazole Magnesium

Esomeprazole sodium (5 g; 13.61 mmol; e.e. of 99.98%), was dissolved in DM water (63 ml) and filtered. To the filtrate, anhydrous MgCl$_2$ (0.648 g; 6.8 mmol) dissolved in DM water (25 ml) was added drop wise and stirred for 1 h. The precipitated product was filtered, washed with DM water and dried under reduced pressure at 40° C. to yield of amorphous esomeprazole magnesium trihydrate.

Yield—4.4 g (85%)

Enantiomeric excess—100%

COMPARATIVE EXAMPLE

Preparation of Esomeprazole BINOL Inclusion Complex

Omeprazole (60 mg; 0.174 mmol) and optical pure BINOL (50 mg; 0.174 mmol) were suspended in toluene (2 ml) and stirred for 36 h at room temperature to yield a solid of 26 mg (47.3%) of the blue inclusion complex of esomeprazole-BINOL.

Enantiomeric excess—11.3%

We claim:

1. An improved process for preparing esomeprazole of Formula I,

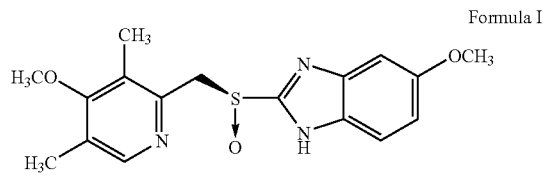 [SMILES: COc1ccc2[nH]c([S@@](=O)Cc3ncc(C)c(OC)c3C)nc2c1]

which comprises :
   a) treating BINOL, omeprazole and an aromatic or polyaromatic phenols at 0-120° C.;
   b) isolating the esomeprazole-BINOL inclusion complex; and
   c) treating the obtained esomeprazole-BINOL inclusion complex in a solvent to give esomeprazole.

2. The process according to claim 1, wherein the aromatic or polyaromatic phenols are selected from the group consisting of phenol, substituted phenol, naphthol and substituted naphthol.

3. The process according to claim 2, wherein substitution on phenol or naphthol is selected from the group consisting of hydroxy, thio, halo, nitro, amino, alkylamino, arylamino, alkyl, cycloalkyl, amido, carboxylic, carboxyl, thioalkyl and thioaryl.

4. The process according to claim 1, wherein step (a) is carried out in the presence or absence of a solvent.

5. The process according to claim 4, wherein the solvent is selected from the group consisting of aprotic solvent, esters, ketones, ethers, nitriles, hydrocarbons, chlorinated hydrocarbons; polar aprotic solvents, dimethylformamide, dimethylsulfoxide; polar solvents, alcohols, water and mixtures thereof.

6. The process according to claim 5, wherein the esters are selected from ethyl acetate, n-butyl acetate; ethers are selected from methyl t-butyl ether, diethylether, dimethylether, diisopropylether, tetrahydrofuran; ketones are selected from acetone, 2-butanone, and 4-methylpentan-2-one; nitriles are selected from acetonitrile; hydrocarbons are selected from benzene, toluene, heptane, hexane; chlorinated hydrocarbons are selected from carbon tetrachloride, methylene dichloride, chloroform; alcohols are selected from methanol, ethanol, propanol, butanol, isopropyl alcohol, 1-propanol.

7. The process according to claim 6, wherein the solvent is toluene.

8. The process according to claim 1, wherein step (c) is carried out in the presence of organic and inorganic base selected from ammonia, triethyl amine, diisopropylethyl amine, sodium bicarbonate, sodium hydroxide, potassium hydroxide; alkali and alkaline earth metal selected from sodium methoxide, lithium methoxide, sodium ethoxide, lithium ethoxide, sodium metal; acid salts selected from sodium acetate, lithium acetate and potassium acetate.

9. The process according to claim 1, wherein the solvent in step (c) is selected from the group consisting of aprotic solvent, selected from esters, ketones, ethers, nitriles, hydrocarbons, chlorinated hydrocarbons; polar aprotic solvents, selected from dimethylformamide, dimethylsulfoxide; polar solvents, selected from alcohols, water and mixtures thereof.

10. The process according to claim 9, wherein the esters are selected from ethyl acetate, n-butyl acetate; ethers are selected from methyl t-butyl ether, diethylether, dimethylether, diisopropylether, tetrahydrofuran; ketones are selected from acetone, 2-butanone, and 4-methylpentan-2-one; nitriles are selected from acetonitrile; hydrocarbons are selected from benzene, toluene, heptane, hexane; chlorinated hydrocarbons are selected from carbon tetrachloride, methylene dichloride, chloroform; alcohols are selected from methanol, ethanol, propanol, butanol, isopropyl alcohol, 1-propanol.

11. The process for preparing esomeprazole according to claim 1, wherein the esomeprazole obtained is further reacted into its salt or hydrate thereof.

12. The process according to claim 11, wherein the esomeprazole is amorphous esomeprazole magnesium trihydrate.

* * * * *